United States Patent [19]

Huber et al.

[11] 4,022,888
[45] May 10, 1977

[54] ESTERIFIED ORGOTEIN

[75] Inventors: Wolfgang Huber, Atherton; Mark G. Saifer, Berkeley; Lewis D. Williams, Menlo Park, all of Calif.

[73] Assignee: Diagnostic Data, Inc., Mountain View, Calif.

[22] Filed: Sept. 9, 1975

[21] Appl. No.: 611,659

[52] U.S. Cl. .......................... 424/177; 260/112 R; 260/113; 260/115; 424/88; 424/287
[51] Int. Cl.² .................. A61K 37/02; A61K 37/14; C07G 7/04
[58] Field of Search ........... 260/112 R, 112 B, 113, 260/115; 424/177, 287

[56] References Cited

UNITED STATES PATENTS

| | | | |
|---|---|---|---|
| 3,687,927 | 8/1972 | Huber | 260/113 |
| 3,758,682 | 9/1973 | Huber | 424/177 |

OTHER PUBLICATIONS

Stansell, J. Biol. Chem., vol. 240, 1965, pp. 4306–4311.
Hartz, J. Biol. Chem., vol. 244, 1969, pp. 4565–4572.
Carrico, J. Biol. Chem., vol. 244, 1969, pp. 6087–6093.

*Primary Examiner*—Albert T. Meyers
*Assistant Examiner*—Anna P. Fagelson
*Attorney, Agent, or Firm*—Millen & White

[57] ABSTRACT

Esterified orgotein, like the native protein, possesses Superoxide Dismutase and anti-inflammatory activity.

10 Claims, No Drawings

ESTERIFIED ORGOTEIN

BACKGROUND OF THE INVENTION

This invention relates to esterified orgotein.

Orgotein is the non-proprietary name assigned by the United States Adopted Name Council to members of a family of water-soluble protein congeners in substantially pure, injectable form, i.e., substantially free from other proteins which are admixed or associated therewith in the sources thereof. U.S. Pat. No. 3,758,682 claims pharmaceutical compositions comprising orgotein.

The orgotein metalloproteins are members of a family of protein congeners having a characteristic combination of physical, chemical, biological and pharmacodynamic properties. Each of these congeners is characterized physically by being the isolated, substantially pure form of a globular, buffer and water-soluble protein having a highly compact native conformation which, although heat labile, is stable to heating for several minutes at 65° C. at pH 4–10. Chemically, each is characterized by containing all but 0–2 of the protein aminoacids, a small percentage of carbohydrate, no lipids, 0.1 to 1.0% metal content provided by one to five grams atoms per mole of one or more chelated divalent metals having an ionic radius of 0.60 to 1.00A., and substantially no chelated monovalent metals or those that are cell poisons in the molecule.

The aminoacid composition of the orgotein congeners is remarkably consistent irrespective of the source from which it is isolated.

Table I lists the distribution of aminoacid residues, calculated for a molecular weight of 32,500 of several orgotein congeners.

subject of the application filed simultaneously herewith entitled "N-alkylated orgotein" (Ser No. 611,657) and are part of the instant invention, whose alkylated groups are limited to —COOH groups and whose free amino groups are primary groups, i.e., unalkylated.

SUMMARY OF THE INVENTION

In a composition aspect, this invention relates to orgotein esters.

In another composition aspect, this invention relates to pharmaceutical compositions comprising the novel orgotein esters of this invention.

In a method of use aspect, this invention relates to the treatment of inflammatory conditions with a composition of this invention.

DETAILED DISCUSSION

The native orgotein protein possesses, inter alia, anti-inflammatory activity. See U.S. Pat. No. 3,758,682. It also possesses uniquely high superoxide dismutase activity. See McCord & Fridovich, J. Biol. Chem., 244, 6,049 (1969); Keele, McCord and Fridovich, J. Biol. Chem., 245, 6,176 (1970); ibid, 246, 2,875 (1971). Suprisingly, the anti-inflammatory activity of the native protein is substantially unaffected by esterification. Accordingly, the esterified proteins are useful in the same manner as the native protein, e.g., for the treatment of inflammatory conditions in mammals and other animals as disclosed in U.S. Pat. No. 3,758,682, whose disclosure is incorporated by reference.

Orgotein congeners contain about 50–68 glutamic and aspartic residues but only about 20–27 of these have free acid groups. Since the orgotein molecule is made up of two identical or almost identical peptide chains (sub-units), half of these aminoacid residues are

TABLE I

AMINO ACID COMPOSITION OF SEVERAL ORGOTEIN CONGENERS
[Residues per mole, M.W. = 32,500]

| Aminoacids | Liver, Beef | Red Blood Cells (RBC) | | | | | | | | | Range |
| | | Beef | Sheep | Horse | Pork | Dog | Rabbit | Rat | Guinea Pig | Chicken | Human | |
|---|---|---|---|---|---|---|---|---|---|---|---|---|
| Alanine | 19 | 19 | 18 | 18 | 18 | 16 | 19 | 22 | 22 | 23 | 22 | 16–23 |
| Arginine | 8 | 8 | 10 | 6 | 8 | 8 | 8 | 7 | 8 | 8 | 8 | 6–10 |
| Aspartic acid | 37 | 36 | 35 | 35 | 31 | 29 | 34 | 30 | 34 | 36 | 37 | 29–37 |
| Cystine-½ | 6 | 6 | 6 | 6 | 6 | 6 | 6 | 6 | 4 | 10 | 8 | 4–10 |
| Glutamic acid | 21 | 23 | 22 | 30 | 28 | 30 | 25 | 38 | 29 | 26 | 28 | 21–38 |
| Glycine | 53 | 52 | 52 | 51 | 52 | 53 | 54 | 54 | 53 | 56 | 51 | 51–56 |
| Histidine | 16 | 16 | 14 | 20 | 16 | 15 | 17 | 20 | 15 | 17 | 14 | 14–20 |
| Isoleucine | 18 | 18 | 18 | 14 | 16 | 18 | 16 | 16 | 18 | 15 | 17 | 14–18 |
| Leucine | 17 | 17 | 17 | 18 | 16 | 16 | 19 | 12 | 17 | 15 | 20 | 12–20 |
| Lysine | 22 | 21 | 23 | 26 | 23 | 20 | 21 | 18 | 20 | 21 | 23 | 18–26 |
| Methionine | 2 | 2 | 2 | 2 | 2 | 6 | 3 | 4 | 2 | 3 | 1 | 1–6 |
| Phenylalanine | 8 | 8 | 7 | 9 | 8 | 8 | 9 | 6 | 8 | 8 | 8 | 6–9 |
| Proline | 12 | 13 | 15 | 10 | 10 | 10 | 13 | 10 | 12 | 13 | 12 | 10–15 |
| Serine | 17 | 17 | 14 | 14 | 13 | 20 | 18 | 18 | 18 | 15 | 19 | 13–30 |
| Threonine | 26 | 25 | 20 | 16 | 27 | 20 | 21 | 17 | 17 | 18 | 18 | 16–27 |
| Tryptophan[1] | Nil | Nil | Nil | Nil | Nil | Nil | Nil | Nil | Nil | 1 | 2 | 0–2 |
| Tyrosine[2] | 2 | 2 | 2 | Nil | 4 | 2 | Nil | 2 | Nil | 2 | Nil | 0–4 |
| Valine | 33 | 32 | 31 | 29 | 29 | 34 | 31 | 35 | 32 | 30 | 30 | 29–35 |
| Total | 317 | 315 | 306 | 304 | 307 | 311 | 315 | 315 | 309 | 317 | 318 | 304–318 |

[1]Colorimetric determination
[2]Average of amino acid analysis and spectrophotometric determination.

It can be seen from Table I that orgotein congeners have from 29–37 aspartic acid and 21–38 glutamic acid groups. The present invention is directed to orgotein derivatives in which at least a portion of these aminoacid residues in free acid form are esterified.

As will be apparent to those skilled in the art, some esterification reagents and conditions are capable of simultaneously alkylating free amino groups in the orgotein molecule and esterifying carboxylic acid groups. Such N-alkylated esterified orgoteins are the in each chain, which are tightly but non-covalently bound together under moderate conditions of temperature and pH. Esterification changes the charge of the orgotein molecule and usually only up to about 10 and preferably up to about 6 to 8 of these free acid groups can be esterified and still retain that conformation of the native molecule, upon which stability and drug utility is dependent.

The carboxylic acid group esterification can be quantitated by counting the charge change shown on electrophoresis. If desired, the esterified orgotein can be hybridized with native orgotein, as described hereinafter, thereby reducing by one-half the number of esterified carboxylic acid groups in the molecule.

Because the orgotein molecule is composed of two identical peptide chains, the ester groups probably are distributed more or less evenly between the two chains. Since a single esterifying agent is ordinarily employed, the ester groups will all be identical. However, it is possible to produce esterified orgoteins having two or more different ester groups in the molecule and even within each chain thereof.

One way of producing a mixed ester of orgotein is by esterifying in stages with different esterifying agents. For example, a fraction of the free acid groups can be esterified with a low concentration of one esterifying agent, e.g., diethyl sulfate, and another fraction of the acid groups esterified with a higher concentration of another esterifying agent, e.g., diazomethane. What constitutes a low or high concentration of esterifying agent will depend on its relative rates of reaction with protein acid groups and with solvent and will thus depend on the reaction pH and on the esterifying agent, and to a lesser extent on buffer and temperature.

Another method of producing a mixed orgotein ester is by hybridization. The term hybridization or orgotein refers to the formation of a mixed orgotein from the subunit chains of two different orgotein molecules, e.g., $A_2$ and $B_2$, A and B being their respective peptide chains. ($A_2 + B_2 \rightleftharpoons 2AB$). The charge of the heterodimer, AB, on electrophoresis should be the average of that of the homodimers $A_2$ and $B_2$, assuming that the same portion of each sub-unit is involved in the binding in all cases.

Methyl orgotein and ethyl orgotein can each be hybridized with native orgotein or with each other by heating with a slight excess of native orgotein at 50° C. for 4 hours. The resulting heterodimers electrophorese as a mixture of bands intermediate between native orgotein and the bands of the esterified orgotein prior to hybridization.

As will be apparent, these hybrid semi-esterified orgotein molecules can be further esterified with a different esterifying agent to produce a hybrid esterified orgotein in which the ester groups in one peptide chain differ from those in the other.

The esterified orgoteins of this invention appear to have essentially the same spatial conformation as the native orgotein molecule. Chelated $Cu^{++}$ and $Zn^{++}$ (Gram Atoms Per Mole) contents are about the same as that of orgotein. Like orgotein, they are highly resistant to Pronase and other proteolytic enzymatic degradation. Superoxide dismutase enzymatic (SOD) activity is not markedly reduced until more than about 6–8 carboxylic acid groups are esterified.

The exact nature of the esterifying groups, like the exact number of esterified groups is not critical as long as the esterifying group is physiologically acceptable. Because of the high molecular weight of the orgotein molecule, even when the orgotein molecule is esterified with esterifying groups of moderate molecular weight, e.g., $\leq 160$, the impact on the overall chemical composition is relatively small, i.e., less than 5%. Of course, the esterification of the free carboxylic acid groups obviously has a profound impact upon the isoelectric point and resulting electrophoretic mobility but, as discussed above, as long as esterification is limited to about 10 or less glutamic and aspartic acid groups, it has no apparent significant effect upon the compact spatial conformation of the molecule and resultant stability, e.g., to heating for 1 hour at 60° C. and to attack by proteolytic enzymes.

As will be apparent, the esterifying group also must be one derived from an esterifying agent capable of esterifying a carboxylic acid group in water or buffer solution, since the reaction is usually conducted therein. Such esterifying agents include dimethyl and diethyl sulfate, diazomethane and other diazo compounds, e.g., of the formula $N_2CH_2COX$ wherein X is, e.g., $OCH_3$, $OC_2H_5$, $NH_2$ or $NHCH_2CONH_2$, and other esters and amides of diazoacetic acid which lack reactive groups, e.g., carboxyl or imino.

For methods of preparing such esters see Methods in Enzymology, Vol. XI, page 612 (1967); K. T. Fry et al, Biochem. Biophys. Res. Comm., 30 489 (1968); G. R. Delpierre and J. S. Fruton, PNAS, 56 1817 (1966).

More particularly, this invention is directed to -COOH esterified orgotein wherein the ester group preferably is of up to 4 carbon atoms, e.g., of a monohydric alkanol, e.g., methyl, ethyl, and most preferably methyl.

Since the exact chemical nature of the ester radical is not critical, as long as it is not physiologically toxic and it can be formed on orgotein's free acid groups, contemplated equivalents of the preferred alkyl esterifying groups described above, insofar as they can be formed, are those bearing one, two or more simple substituents, e.g., halo, alkoxy, carb-alkoxy, carbamido, etc., especially those wherein the ester group bearing the substituent or substituents is methyl. Thus, in addition to esterified orgotein in which the esterified acid groups are $-COOCH_3$, contemplated equivalents are those wherein the ester groups are $-COOR$ where R is $-CH_2COX$ in which X is $OCH_3$, $OC_2H_5$, $NH_2$, $NHCH_2CONH_2$ or $CH_2CH_2-$phenyl, or wherein R is $CH(phenyl)_2$.

Esterification of the $-COOH$ groups can be followed by counting the charge change shown on electrophoresis compared to native orgoteins.

As is known, the electrophoretic mobility of an ion is a function of the electric field strength, net charge of the ion (including conterions), and frictional coefficient. See, for example, C. Tanford "Physical Chemistry of Macromolecules" Wiley, New York (1966). Since the frictional coefficient is dependent on molecular size and shape, and on the solution composition, comparisons of different proteins are not informative. However, by comparing proteins of similar size and shape, in this case orgotein molecules chemically modified with relatively small groups, under identical electrophoresis conditions, the only variable affecting this electrophoretic mobility is net charge.

Comparison of the electrophoretic patterns of a number of chemically modified orgotein molecules is consistent with this conclusion. Native bovine orgotein electrophoreses mainly as one band (band 1), with minor amounts of faster moving bands (bands 2, 3, etc.) equally spaced ahead of the main band, representing orgotein molecules with a higher ratio of $-COOH$ to $-NH_2$ groups than those molecules forming band 1. Esterification of successively higher numbers of the free $-COOH$ groups of the native bovine orgotein leads to the formation of a series of successively more cathodic (migrating toward the negative electrode)

electrophoretic bands as successively more free carboxylic acid groups of the orgotein molecule are esterified.

A graph of distance electrophoresed versus band number is relatively linear at low extents of —COOH modification but curves gradually at higher modification, since there is a limit to how fast even the most highly charged species can move through solution. The faster migrating species are also more sensitive to salt concentration, and are appreciably retarded when salt-containing samples are electrophoresed. Therefore, since extrapolating more than about two band positions in not always precise, accurate charge counting requires that the unknown be co-electrophoresed with a solution which contains all the bands from 1 through the position of interest (e.g., partially acetylated orgotein).

All the conventional protein modification reactions which have been applied to the orgotein molecule so far have been consistent with this interpretation, viz., the band positions correspond to integral charge changes from the native orgotein molecule. Esterification with dimethylsulfate or with ethyl diazoacetate gives bands −1, −2, −3, −4, etc., indicating that 1, 2, 3, and 4, respectively, free carboxylic acid groups have been chemically modified.

Generally speaking, at most only about eight of the free —COOH groups can be esterified without deleterious effects. Attempts to esterify more than 6–8 —COOH groups, i.e., to esterify more than three —COOH groups of each of the two orgotein peptide sub-units, usually leads to denaturation and loss of superoxide dismutase activity.

As would be expected, the distribution of the esterifying alkyl groups on the orgotein molecule probably is random since none of the titrable free carboxy groups appear abnormally readily esterifiable. Because the orgotein molecule is composed of two identical peptide chains, the ester groups of a partially esterified orgotein will be distributed more or less randomly along each peptide sub-unit but more or less evenly between the two chains. Since a single esterifying agent is ordinarily employed, the ester groups will all be identical. However, it is possible to produce esterified orgoteins having two or more different ester groups in the molecule and even within each chain thereof.

One way of producing a mixed esterified orgotein is by esterifying in stages with different esterifying agents. For example, a portion of the free —COOH groups can be esterified with one esterifying agent, e.g., dimethyl sulfate, and the remainder of the reactive —COOH groups esterified with another esterifying agent, e.g., ethyl diazoacetate.

Another method of producing a mixed esterified orgotein is by hybridization. The term hybridization of orgotein refers to the formation of a mixed orgotein from the sub-unit chains of two different orgotein molecules, e.g., $A_2$ and $B_2$, A and B being their respective peptide chains. ($A_2 + B_2 \rightleftharpoons 2AB$). The charge of the heterodimer, AB, on electrophoresis should be the average of that of the homodimers $A_2$, and $B_2$, assuming that the same portion of each sub-unit is involved in the binding in all cases.

Methyl esterified orgotein, produced by esterifying about 6 free acid groups of the orgotein molecule with dimethyl sulfate and carboxymethyl esterified orgotein, produced by esterifying the native orgotein molecule with ethyl diazoacetate, can each be hybridized with native orgotein or with each other by heating together at 50° C. for 4 hours.

In addition to the esterified bovine orgoteins of the examples hereinafter, other examples of esterified bovine orgoteins of this invention are carbomethoxymethyl orgotein and carbamylmethyl orgotein, wherein in each instance there are 3–4 such esterified groups in each of the two sub-units of the orgotein molecule and the corresponding esterified orgoteins wherein there are 1 or 2 such ester groups in each such sub-unit, respectively, and the corresponding human, sheep, horse, pork, dog, rabbit, guinea pig and chicken congeners of each of these.

The esterified orgotein can be isolated from the reaction solution, preferably after dialysis to remove extraneous ions, by conventional lyophilization, e.g., in the manner described in U.S. Pat. No. 3,758,682. If desired, the esterified orgotein can first be purified by ion exchange resin chromatography, electrophoresis and-/or gel filtration employing a polymer which acts as a molecular sieve.

Filtration through a micropore filter, e.g., "Millipore", in a conventional manner into sterile vials, optionally after adjusting ionic strength with NaCl and-/or sodium phosphate, e.g., to isotonicity, will provide a sterile solution suitable for administration by injection.

The pharmaceutical compositions of this invention comprise an orgotein ester of this invention and a pharmaceutically acceptable carrier. The form and character which this carrier takes is, of course, dictated by the mode of administration.

The pharmaceutical composition preferably is in the form of a sterile injectable preparation, for example, as a sterile injectable aqueous solution. The solution can be formulated according to the known art using those carriers mentioned above. The sterile injectable preparation can also be a sterile injectable solution or suspension in any non-toxic parenterally acceptable diluent or solvent, or can be a lyophilized powder for reconstitution with such solvent.

The compositions of this invention combine an effective unit dosage amount of an orgotein ester of this invention, i.e., the orgotein ester is present at a concentration effective to evoke the desired response when a unit dose of the composition is administered by the route appropriate for the particular pharmaceutical carrier. For example, liquid compositions, both topical and injectable, usually contain about 0.5 to 20 mg. of orgotein ester per 0.25 to 10 ml., preferably about 0.5 to 5 ml., except I.V. infusion solutions, which can also be more dilute, e.g., 0.5 to 20 mg. orgotein ester per 50–1,000 ml., preferably 100–500 ml of infusion solution. Tablets, capsules and suppositories usually contain 0.1 to 25 mg., preferably 1 to 10 mg., of orgotein ester per unit.

Esterified orgotein usually is administered by instillation or by injection, e.g., intramuscularly, subcutaneously, intravenously or intradermally. I.M. is preferred, except in case of shock where I.V. is sometimes preferred for more rapid onset of effect, and in certain localized disorders, e.g., radiation and other cystitis, where local injection, infusion and/or instillation is often more effective. Individual doses usually fall within the range of 0.5 to 20 mg. The preferred range for humans is about 0.5 to 8 mg.: for horses, about 5.0 − 10.0 mg. The exact dosage is not critical and depends on the type and the severity of the disease.

Esterified orgotein, like orgotein, is effective in treating a wide variety of inflammatory conditions, including those in which synthetic anti-inflammatory agents have limited utility, e.g., because of toxic side effects upon prolonged use.

More specifically, esterified orgotein is efficacious in ameliorating inflammatory conditions and mitigating the effects thereof, for instance those involving the urinary tract and the joints, in various mammals. It is useful in alleviating the symptoms associated with rheumatoid, osteo and post-traumatic arthritis, as well as bursitis, tendonitis etc.

For further details relating to how to isolate the starting orgotein congeners and how to use the esterified orgotein of this invention, including modes of administration, dosage forms, dosage regimen and inflammatory and other conditions susceptible to treatment with esterified orgotein, see U.S. Pat. No. 3,758,682, whose disclosure is incorporated by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1: Methyl Esterification

A solution (125 μg/ml) of 0.5 mg bovine orgotein and 0.5% vol/vol of dimethyl sulfate in 4 ml. of 0.05 M acetate buffer is maintained at pH 5 for 100 min. Electrophoretic analysis of the reaction product showed SOD active bands from +1 through −6 (average −4). The product is orgotein having an average of 4 —COOCH$_3$ groups.

EXAMPLE 2: Methyl Esterification

A solution of 0.5 mg. bovine orgotein an 10 μl dimethyl sulfate in 4 ml. water was kept at constant pH by addition of 0.1 M NaOH. The rate of base uptake in the pH range 7–10 was fairly independent of pH and of the addition of 0.25 mole sodium phosphate buffer. Electrophoresis showed the formation of more cathodic SOD-active bands at an initial rate of about −0.5 charge/hour. After 21 hours, predominantly at pH 7–8, the solution was analyzed for N-methylation and for esterification, as described below. N-Methylation could not be detected.

a. Acetylation of a 0.5 ml. aliquot of the esterified orgotein with 1 μl acetic anhydride +3 μl 6M NaOH at 4° C., gave a solution whose electrophoresis pattern was a fast-moving anodic band similar to that of acetylated native orgotein, thus establishing that the free amino groups were unaffected during the esterification.

b. A 1 ml. aliquot of the esterified orgotein solution was adjusted to pH 10.5 and stored covered in a dessicator with NaOH pellets. Although the cathodic band pattern of bands 1 through −4 was stable at pH 7–9, at pH 10.5 the cathodic bands gradually disappeared over a period of 4 days as the electrophoretic pattern of native orgotein reappeared. Protein methyl esters commonly hydrolyze readily at alkaline pH's, thus confirming the more cathodic bands appearing after the esterification were orgotein esters.

From the foregoing it is apparent that after two hours, dimethyl sulfate at pH 7–10 esterified an average of one —COOH group per molecule; after four hours, about 2 per molecule; and continues thereafter to increase the number of esterified —COOH groups to a maximum of about 6 per molecule.

Following the procedure of Examples 1 and 2, employing, respectively, the corresponding human, sheep, horse, pig, dog, rabbit, guinea pig and chicken orgotein congeners as starting materials, in each case, an average of about four carboxylic acid groups of the orgotein molecule are converted to methyl esters thereof.

Following the procedure of Example 1 and 2, employing diethyl sulfate instead of dimethyl sulfate, orgotein esters having from one to six free carboxylic acid groups converted to ethyl esters thereof are produced. The properties of the resulting esterified orgoteins are essentially the same as the methyl esterified orgotein.

The esterified orgoteins can be further purified, if desired, by ion exchange chromatography to separate from each other the species of different net charge and, hence, different extents of esterification. For example, elution of 200 mg orgotein through a 2.5 × 40 cm DEAE Sephadex column with 4 liter of a 0.01 M to 0.2 M linear gradient of tris pH 8.5 buffer separates the orgotein bands from each other, the electrophoretically more cathodic bands eluting first. By such a procedure, the mixture of methyl esterified orgoteins produced by the procedure of Example 1 can be separated into fractions containing predominantly 1, 2, 3, 4, 5 or 6 methyl ester groups per orgotein molecule.

Such fractionation of a partially modified orgotein by ion-exchange chromatography is applicable to any modified orgotein whose molecular charge depends upon the extent of modification; e.g., methyl esterfied orgotein, carbethoxymethyl esterified orgotein, and N-acetylated orgotein.

EXAMPLE 3: Carbethoxymethyl Esterification

Ethyl diazoacetate is prepared by reaction of glycine ethyl ester with nitrous acid, as in "Organic Synthesis" Coll. Vol. IV, p. 424, but using CCl$_4$ rather than CH$_2$Cl$_2$ to extract the ethyl diazoacetate from aqueous solution.

Two ml. of the approximately 1M ethyl diazoacetate/CCl$_4$ solution are placed in a 25 ml. flask and most of the CCl$_4$ is evaporated under aspirator pressure. A solution of 9 mg. bovine orgotein/3 ml. water is added and swirled to disperse the organic phase. The solution is stored at 4° C. and swirled every few days. The reaction mixture remains heterogeneous throughout. Electrophoresis shows the gradual formation of more cathodic SOD active protein bands −1 through −6. The average charge change is 1.2 after 5 days and 3 after 12 days. The product is a mixture of carbethoxymethyl orgotein esters having after 5 days either one or two such ester groups per molecule, and after 12 days, from 1 through 6 such ester groups.

The aqueous phase is then filtered and desalted by chromatographic fractionation employing a 10 cc Sephadex G-25 column. The protein fractions are lyophylized and redissolved in 2 ml. of water, and the pH raised from 3.7 to 5.6 with 2 μl 1M NaOH. Electrophoresis shows no change from before desalting and lyophylization. Re-reaction of this solution for a month under the same conditions as above gives a smear of protein on electrophoresis with less SOD activity and no material more cathodic than band −6.

EXAMPLE 4: Methyl Esterification

Following the procedure of Examples 1 and 2, bovine orgotein was alkylated under the conditions set forth in the table below.

|  | pH | Buffer | Orgotein | Dimethyl Sulfate % by vol | Hydrolysis Half-time* | SOD Active Bands on Electrophoresis |
|---|---|---|---|---|---|---|
| (a) | 5.0 | 0.5 M acetate | 125 µg/ml. | 0.25 | 54 min. | +1 through −4 (avg.−2) |
| (b) | 5.0 | acetate | 125 µg/ml. | 0.5 | 54 min. | −1 through −6 (avg.−4) |
| (c) | 7.0 | 0.016 M phosphate | 80 " | 0.65 | 1 hr. | −2 through −6 |
| (d) | 7.0 | phosphate | 80 " | 1.3 | 1 hr. | faint streak of SOD from +4 to −6, peaking at −6 position |
| (e) | 11.2–9.3 | 0.05 M carbonate | 125 " | 0.5 | ½ hr. (at pH 10) | +2 to −3 |

*Half-time for NaOH uptake needed to maintain constant pH.

The product of Example (a) has an average of 2 esterified —COOH groups per molecule and Example (b), an average of 4 such groups. The presence of a plurality of cathodic bands establishes that the esterified products consist of a plurality of esterified orgoteins containing from one up to about 6 ester groups per molecule.

EXAMPLE 5: Methyl Ester/N-Acetyl Hybrid

To a solution of (125 µg/ml) of 0.5 mg methyl esterified orgotein, produced by the procedure of Example 1, was added 0.5 mg completely N-acetylated orgotein. Electrophoresis of the mixture showed only the bands corresponding to methyl esterified orgotein plus the anodic band corresponding to N-acetyl orgotein. After the mixture was heated at 50° C for 4 hours, however, electophoresis showed the formation of several new species (at band positions +7 to +11) and over 50% diminution of the original N-acetyl and methyl ester orgotein bands.

The new species formed by heating the mixture of modified orgoteins are hybrids (heterodimers) containing one submit each of N-acetyl orgotein (containing 10 N-acetyl lysines per subunit) and of methyl esterified orgotein (containing 0 to 3 —COOMe groups per subunit).

The hybrids can be isolated from their equilibrium mixture with the N-acetyl and —COOMe orgoteins (homodimers) by ion exchange chromatography at low temperature, as described in Example 2. The isolated heterodimers on storage can continue to re-hybridize to reform a mixture containing both homodimers as well. The rate of re-hybridization is dependent on temperature and is low at low temperatures.

The preceeding examples can be repeated with similar success by substituting the generically or specifically described reactants and/or operating conditions of this invention of those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An esterified orgotein wherein up to 8 of the free carboxylic acid groups of the orgotein protein molecule are esterified with a physiologically acceptable group, and the esterified acid groups are -COOR, wherein R is alkyl of 1–4 carbon atoms, $CH(phenyl)_2$ or —$CH_2COX$, wherein X is $OCH_3$, $OC_2H_5$, $NH_2$, $NHCH_2CONH_2$ or $CH_2CH_2$ phenyl.

2. The orgotein ester of claim 1, wherein the orgotein is bovine.

3. The orgotein ester of claim 1, having from 1 to 6 esterified carboxylic acid groups per molecule.

4. The orgotein ester of claim 3, wherein the orgotein is bovine.

5. The orgotein ester of claim 1, wherein the esters are alkyl esters of 1 to 4 carbon atoms.

6. The orgotein ester of claim 1, wherein the esters are methyl esters.

7. The orgotein ester of claim 6, wherein the orgotein is bovine.

8. The orgotein ester of claim 6, having from 1 to 6 esterified carboxylic acid groups per molecule.

9. A pharmaceutical composition having antiinflammatory activity comprising, in admixture with a pharmaceutically acceptable carrier, an anti inflammatorily effective amount per unit dosage of an orgotein ester of claim 1.

10. The pharmaceutical composition according to claim 9. in sterile injectable form.

* * * * *